United States Patent
Koebel et al.

(10) Patent No.: US 9,737,440 B2
(45) Date of Patent: Aug. 22, 2017

(54) ABSORBENT ARTICLES HAVING VARIABLE DATA THEREON AND SYSTEMS AND METHODS FOR PRINTING SUCH ARTICLES

(75) Inventors: Martin Koebel, Bloomington, IL (US); Craig E. Krone, Mankato, MN (US); Ron Hoffmeyer, Dana Point, CA (US)

(73) Assignee: Taylor Corporation, North Mankato, MN (US)

( * ) Notice: Subject to any disclaimer, the term of this patent is extended or adjusted under 35 U.S.C. 154(b) by 12 days.

(21) Appl. No.: 13/595,172

(22) Filed: Aug. 27, 2012

(65) Prior Publication Data
US 2013/0052432 A1 Feb. 28, 2013

Related U.S. Application Data

(60) Provisional application No. 61/527,939, filed on Aug. 26, 2011, provisional application No. 61/534,720, filed on Sep. 14, 2011.

(51) Int. Cl.
*B41J 2/165* (2006.01)
*A61F 13/15* (2006.01)
(Continued)

(52) U.S. Cl.
CPC .............. *A61F 13/15* (2013.01); *B41J 3/407* (2013.01); *B41J 11/0085* (2013.01);
(Continued)

(58) Field of Classification Search
None
See application file for complete search history.

(56) References Cited

U.S. PATENT DOCUMENTS

| 4,378,391 A | 3/1983 | Allen |
| 5,213,037 A | 5/1993 | Leopardi, II |

(Continued)

FOREIGN PATENT DOCUMENTS

| DE | 102006018546 A1 | 10/2007 |
| DE | 10 2012 015 838 A1 | 2/2014 |

(Continued)

OTHER PUBLICATIONS

The Stationary Studio printout, circa Apr. 2013, 5 pages.
(Continued)

*Primary Examiner* — Alejandro Valencia
(74) *Attorney, Agent, or Firm* — Patterson Thuente Pedersen, P.A.

(57) ABSTRACT

Printed articles having unique data thereon, and flexible substrate printing systems and methods that allow for customization of flexible, absorbent substrates. Customization is accomplished by printing variable data on substrate stock in a single run or production pass such that at least some of the articles in a set of articles contains printed matter different from printed matter on other articles in the same set. The substrate stock can include napkin material, toilet tissue material, paper towel material, or any other similar substrate. One or more print engines are configured to receive substrate stock from the conveyor and print variable matter on the substrate stock. The methods and systems allow for economical and efficient production of small or large customer orders without the need to produce individual printing dies or plates.

13 Claims, 4 Drawing Sheets

(51) Int. Cl.
  *B42D 15/00* (2006.01)
  *B41M 5/00* (2006.01)
  *B41J 3/407* (2006.01)
  *B41J 11/00* (2006.01)
  *G06T 11/20* (2006.01)

(52) U.S. Cl.
  CPC ....... *B41M 5/0047* (2013.01); *B42D 15/0093* (2013.01); *G06T 11/203* (2013.01); *Y10T 428/24802* (2015.01)

(56) References Cited

U.S. PATENT DOCUMENTS

| | | | |
|---|---|---|---|
| 5,753,331 | A | 5/1998 | Jeffrey |
| 5,766,389 | A | 6/1998 | Brandon et al. |
| 6,354,212 | B1 | 3/2002 | Krinsky |
| 6,467,410 | B1* | 10/2002 | Rasmussen et al. ....... 101/424.1 |
| 6,477,948 | B1 | 11/2002 | Nissing et al. |
| 6,533,324 | B2* | 3/2003 | Zorn ................................ 283/56 |
| 6,698,877 | B2 | 3/2004 | Urlaub et al. |
| 6,764,577 | B2 | 7/2004 | Burazin et al. |
| 6,928,929 | B1 | 8/2005 | McNeil |
| 6,929,838 | B1 | 8/2005 | McNeil |
| 6,957,884 | B2 | 10/2005 | Sharma et al. |
| 7,016,865 | B1 | 3/2006 | Weber et al. |
| 7,871,492 | B2 | 1/2011 | Bakken et al. |
| 7,871,498 | B2 | 1/2011 | Bakken et al. |
| 2002/0152001 | A1* | 10/2002 | Knipp et al. ................... 700/100 |
| 2003/0004824 | A1* | 1/2003 | Joshi et al. ...................... 705/26 |
| 2004/0003521 | A1 | 1/2004 | Penn et al. |
| 2004/0058130 | A1 | 3/2004 | Nissing |
| 2004/0131842 | A1 | 7/2004 | Urlaub et al. |
| 2004/0143231 | A1 | 7/2004 | Nair et al. |
| 2004/0163784 | A1 | 8/2004 | Urlaub et al. |
| 2004/0258887 | A1 | 12/2004 | Maciag et al. |
| 2004/0261639 | A1 | 12/2004 | Vaughn et al. |
| 2005/0015066 | A1 | 1/2005 | Anderson et al. |
| 2005/0133387 | A1 | 6/2005 | Cohen et al. |
| 2005/0153100 | A1 | 7/2005 | Zoller et al. |
| 2006/0070701 | A1 | 4/2006 | Kobayashi et al. |
| 2007/0164554 | A1 | 7/2007 | Krone et al. |
| 2007/0239126 | A1 | 10/2007 | Wilson et al. |
| 2009/0028586 | A1* | 1/2009 | Yamashiro ............ B41J 11/006 399/18 |
| 2010/0213699 | A1 | 8/2010 | Tremper |
| 2010/0264591 | A1 | 10/2010 | Hutchison et al. |
| 2011/0147445 | A1 | 6/2011 | Horn et al. |
| 2012/0209688 | A1 | 8/2012 | Lamothe et al. |

FOREIGN PATENT DOCUMENTS

| | | |
|---|---|---|
| EP | 1242247 A1 | 9/2002 |
| EP | 2 926 995 A1 | 10/2015 |
| WO | WO 01/36209 A1 | 5/2001 |
| WO | WO 2007/075569 A2 | 7/2007 |

OTHER PUBLICATIONS

ScanNap printout, circa 2011, 1 page.
PCT Search Report dated Nov. 21, 2012 for PCT Application No. PCT/US2012/052250 filed Aug. 24, 2012, 5 pages.
International Preliminary Report on Patentability and Written Opinion for PCT Application No. PCT/US2012/052250 filed Aug. 24, 2012, 6 pages.

* cited by examiner

ABSORBENT ARTICLES HAVING VARIABLE DATA THEREON AND SYSTEMS AND METHODS FOR PRINTING SUCH ARTICLES

RELATED APPLICATIONS

The present application claims the benefit of U.S. Provisional Application No. 61/527,939 filed Aug. 26, 2011 and U.S. Provisional Application No. 61/534,720 filed Sep. 14, 2011, both entitled SYSTEMS AND METHODS FOR PRINTING OF ABSORBENT SUBSTRATES WITH VARIABLE DATA, and each of which is incorporated herein in its entirety by reference.

FIELD OF THE INVENTION

The present invention relates generally to printed absorbent substrates, and more particularly, to digital printing on absorbent substrates, such as paper napkins, with variable data.

BACKGROUND OF THE INVENTION

Flexible, absorbent substrates are used in many everyday items, like tissue items such as napkins and paper towels. Many occasions or events provide for the personalization of such items. For example, personalized wedding napkins can add an accent to the theme of a wedding reception. Personalized wedding cocktail napkins can feature, for instance, the date of the wedding, the bride's and groom's names or initials, or a meaningful quote or expression, and are something that is highly impactful on the wedding reception guests. It can also be highly desirous to have personalized napkins at other occasions and events, like birthday parties, business events, or baby showers, for example.

Generally, in traditional printing systems, the personalization of flexible substrates is limited to a single uniform or static print on the substrate in that the same exact print is repeated on each and every napkin within the print run. Thus, the level of data is non-variable between substrates of the same run or production pass, i.e. it is non-variable data. In the wedding reception example described above, a single production pass can create the napkins for the wedding reception. However, implementing differing details between subsets of the production run of napkins is infeasible without doing a secondary production run. For example, napkins cannot be generated in the same production run for a certain subset of guests (e.g. a groom's friends) that contain unique information, such as a photo or graphic, message or quote directed to the subset of guests with different information for another subset of guests (e.g. the bride's parents). Likewise, a set of napkins, each napkin having unique information, such as the name of an individual guest printed on it, similarly cannot be generated in the same production run.

Traditionally, printed absorbent substrates, such as napkins, are produced either on letterpress equipment using dies or polymer plates, or through the use of flexographic printing, screen printing, or di-sublimation heat transfer. In the case of processes utilizing letterpress equipment, the production of a die or plate is required, which can be expensive to produce for even a single run of printing where all of the printed matter is uniform. Further, in the case of the variable data described above, creating a die or plate for each iteration of variable data is impractical. In the case of the flexographic, screen, or di-sublimation techniques, equipment components also vary, depending on the information to be printed. Additionally, the size of the substrates and desired size of the printed material can vary, even within the materials for the same event or occasion. Beverage-size, luncheon-size, and dinner-size napkins, as well as the printing prior to or after conversion, further affects the equipment used in the various traditional processes. For example, the printing of converted napkins using traditional processes can result in poor printing quality and/or registration and is limited to static print with no means to apply variable data at an economical cost.

Thus, there remains a need for systems and methods of printing on absorbent substrates which can produce a high-quality printed substrate having personalized, varied data between pieces in a single production run.

SUMMARY OF THE INVENTION

The systems and methods of the present application substantially meet the aforementioned needs of the industry. The present invention provides embodiments of an absorbent substrate printing system and methods capable of printing varied data among a single production run, eliminating make ready setups for separate runs, such as change-out or reconfiguration of any of printing plates or dies, materials including inks and substrates, data to be printed, and/or combinations thereof.

The absorbent substrate printing system and methods according to embodiments of the present invention allows for the personalization of absorbent substrates. Thus, personalized matter can be printed on a stock of absorbent substrates that is chosen, such as facial tissue, tissue paper, napkins, or paper towels. Further, embodiments of the present invention allow for the personalization of absorbent substrates by printing variable data on the substrate stock in a single run or production pass such that at least some of the individual substrate stock contains printed matter different from printed matter on other individual substrate stock. Therefore, in an embodiment of substrate stock comprising wedding napkins, a subset of unique napkins can be generated in the same production run for a first subset of guests that contains unique printed information, such as text, graphics, photos, symbols, or the like, as napkins with different unique information for a second subset of guests. Further, a set of napkins can be generated, in the same production run, which includes unique information, such as the name of each individual guest, on a different napkin.

An advantage of embodiments of the present invention is that multiple orders during a single production run is more economically and technically feasible. For example, a gang run, in which multiple (and different) customer orders are printed during a single run or continuously in series by combining several orders right after each other, is easily and efficiently run because the data for each customer order can easily be converted based on programming commands, while only requiring a single production run or minimal changeover (e.g. change of stock) between orders. Furthermore, all of the data required for the gang run is contained in a single batch file that is streamed to the print head. These are advantages over traditional printing systems because to run multiple orders in a single run, the time and costs required to calculate ideal gang run impositions can be cost prohibitive, and often times the ability to gang run jobs is unavailable or infeasible.

Another feature and advantage of embodiments of the present invention is that no plate or die is required. In embodiments, a digital (e.g. ink jet), and non- or low-impact print engine comprising a singular or multiple print heads combined in an array prints onto the substrate. Therefore, production costs are reduced, as no expensive plate or die needs to be created. Production costs are further reduced between production runs, as no plate or die needs to be switched out for each variable data element printed on the substrate. Additionally, because no switching of plates or dies is required, the production process is faster and more efficient.

Another feature and advantage of embodiments of the present invention is that the printed napkins no longer have the printing die impressions left from the pressure of the die hitting the flexible substrate. Also, because the impression of the die hitting the flexible substrate is eliminated, there is less "waste" because fewer napkins, for example, are ripped or receive tears during production. Furthermore, the impression from the dies would sometimes result in the layers of the flexible substrate "sticking" together, resulting in the user of the napkin experiencing difficulty in opening the napkin (the faces of the napkin would be stuck together). The elimination of this impression leaves the napkins without die marks, fluffier, and easier to open and use.

Another feature and advantage of embodiments of the present invention is that the personalized printing can be done before and/or after the conversion of the napkin or tissue product. In an embodiment, napkins are converted, i.e. folded, embossed to add ruffles or other non-printed patterns, and cut into the final napkin form, before they are printed. In another embodiment, raw stock material, such as in the form of a roll or web, is printed prior to being folded and cut. In this embodiment, subsequently, roll material is printed prior to the conversion process into the final napkin form.

Another feature and advantage of embodiments of the present invention is the combining of ink jet printing onto porous flexible substrate stock, like napkin stock. This allows for high-quality printing to be achieved on substrates that are traditionally difficult to print. By offering high-quality printing, indicia that has not previously been successfully printed on porous or absorbent substrates due to bleeding of the ink and the limitations of dies or plates can now be used. Such indicia can include, for example, small text, high-quality images such as photos or graphics, graphics or text incorporating intricate designs, patterns, and/or colors, 2D codes such as QR codes, barcodes, including variable designs, patterns and colors from substrate to substrate/napkin to napkin, and the like.

Another feature and advantage of embodiments of the present invention is the printing of absorbent substrate stock with digital technology. As mentioned above, in embodiments, a digital ink jet non-impact or low-impact printer produces the print on the substrate. In another embodiment, a laser printer creates the printed matter on the substrate. Other digital printing technologies are also considered and the invention is not limited to those discussed herein.

Because the printing process is digital whereby there are no plates or dies, and the data can be varied among a single production run, the quantity of a single production run can be from one into the millions all containing similar or variable print elements. In addition, one or more customer orders can be run in batch mode (i.e. gang-run) eliminating make ready setups for separate runs, thereby reducing cost, time, etc. Further, the digital printing is not limited by the size of the substrate stock, but only by the size of the print head. Therefore, by utilizing an array of print heads, the print size is virtually unlimited. Differing print heads can be utilized in order to change the print area. The printed matter can be a unique image, pattern, code, text, 2D code, barcode, other graphical elements, or any combination thereof.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
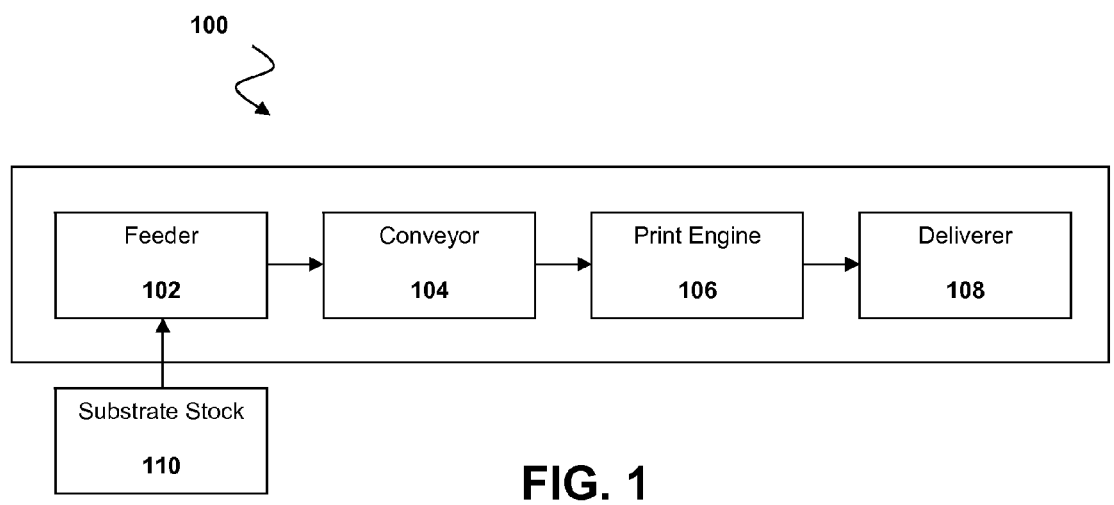
FIG. 1 is a block diagram of a flexible substrate printing system according to an embodiment of the invention.

While the invention is amenable to various modifications and alternative forms, specifics thereof have been shown by way of example in the drawings and will be described in detail. It should be understood, however, that the intention is not to limit the invention to the particular embodiments described but rather to include all modifications, equivalents, and alternatives.

DETAILED DESCRIPTION OF THE DRAWINGS

In an embodiment, a flexible, absorbent substrate printing system is shown generally at 100 in FIG. 1. Printing system 100 generally comprises one or more optional feeders 102, a conveyor or transport device 104, one or more print stations or engines 106, one or more optional cure stations (not shown), and one or more deliverers 108.

Substrate stock 110 generally comprises the material on which the printing is done. Substrate stock 110 can therefore comprise napkin material, toilet tissue material, facial tissue material, tissue paper material, paper towel material, or any other similar absorbent or porous substrate in either web or discrete/batch format. In an embodiment, substrate stock 110 comprises converted stock that is printed when substrate stock 110 is in an unfolded form, a partially-folded form, or a final folded form.

Feeder 102 comprises a receiver configured to receive substrate stock 110 and a transporter configured to place substrate stock 110 on transport device 104. Feeder 102 can comprise any of a variety of suitable feeders for placing substrate stock 110 on transport device 104 or other transport device, such as, for example, continuous feeders, vacuum feeders, stream feeders, friction feeders, top and bottom feed feeders, carriage feeders, or combinations thereof. In one embodiment (not shown), more than one feeder is incorporated into the system to increase throughput. In this case, each feeder can alternately and/or simultaneously place a piece onto the conveyor. For example, one feeder can place product on the conveyor while another is returning to a stock supply to reload, and/or each feeder can simultaneously place pieces on the conveyor.

In an alternative embodiment directed to unconverted raw stock in web format, feeder 102 is substituted for an unwind system.

Transport device 104 can include, for example, a receiver configured to receive substrate stock 110 from feeder 102 and a means for transporting or transporter configured to move substrate stock 110 to print engine 106, or other means for transporting the substrate stock to the print engine. In an embodiment, transport device 104 comprises a conveyor. In one particular non-limiting example, transport device 104 comprises a vacuum conveyor. In such an embodiment, transport device 104 includes a perforated belt or drum and an air drawing element. The air drawing element is positioned underneath the perforated belt such that when substrate stock 110 is placed on the perforated belt or drum, air is drawn through the perforations to substrate stock 110, thereby holding substrate stock 110 substantially flat and in place on the perforated belt or drum. The air drawing element can be configured for different pressures, vacuum area, and vacuum sources for varying types of substrate stock 110. Likewise, varying perforations can be created in the perforated belt or drum.

In an alternative embodiment of printing system 100, transport device 104 is not required. In such an embodiment, feeder 102 is configured to receive substrate stock 110 and subsequently transport substrate stock 110 to print engine 106 similar to operation with transport device 104.

Figure 2:
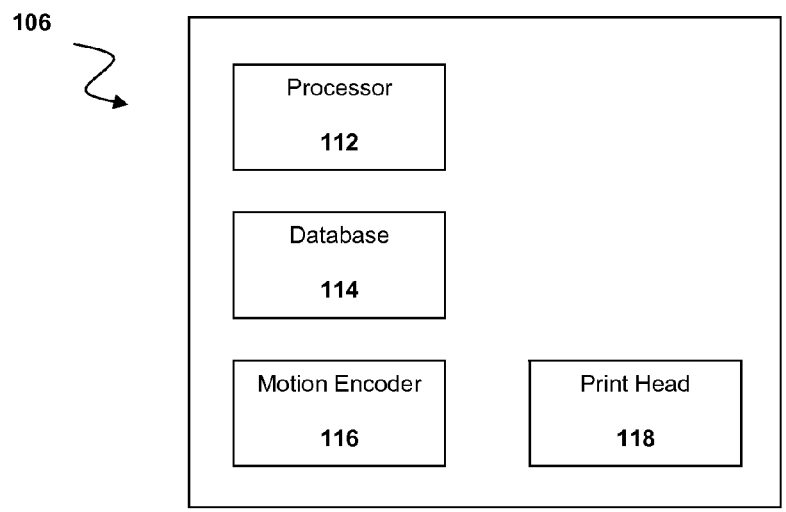
FIG. 2 is a block diagram of the print engine of FIG. 1.

Referring to FIGS. 1-2, print engine 106 is configured to receive substrate stock 110 from transport device 104 and print variable matter onto substrate stock 110. Print engine 106 can utilize any of a variety of digital or non-impact or low-impact printing techniques, such as, for example, ink jet (liquid or solid) such as drop-on-demand or continuous, laser, thermal-transfer, wet/dry toner systems such as xerographic, and the like. In an embodiment, print engine 106 comprises a processor 112, database 114, motion encoder 116, and print head 118. Print head 118 corresponds to the printing technique utilized and can include piezoelectric or thermal heads, for example, in the case of drop on demand technologies. Suitable print engines 106 and/or print heads 118 can include, for example, but not limited to, those commercially available from Xaar of Marietta, Ga., Dimatix, Inc. (Fujifilm) of Santa Clara, Calif., Fuji Xerox of Japan, Eastman Kodak of Rochester, N.Y., Hewlett Packard of Palo Alto, Calif., MemJet of San Diego, Calif., Kyrocera of Japan, and Epson of Long Beach, Calif.

Processor 112 is configured to transmit and receive data related to matter to be printed by print head 118. Processor 112 is further configured to store and retrieve data, in database 114, related to matter to be printed. Processor 112 can further convert a source file, such as an order file supplied by a customer, or a plurality of orders to be run in a single run, to a print-ready file, such as PDF, PostScript of PRL format file depending on the print driver being used. Additionally, processor 112 is further configured to receive data from motion encoder 116 to determine when substrate stock 110 is under print head 118.

Database 114 is configured to store data, such as source files, related to matter to be printed by print head 118. In an embodiment, database 114 comprises a digital source file. In another embodiment, database 114 comprises a plurality of files for a production run. In another embodiment, database 114 comprises a more traditional database, such as, for example, a relational database or a blob database. Database 114 can store images, text, 2D codes, barcodes, or any other graphical element that may be desirous to print. Database 114 can store sequences of data for a single production run such that during the run, the data transmitted to print head 118 by processor 112 is variable. Database 114 can be populated using customer supplied files entered by a user such as an operator, or can be populated by a customer directly, such as through a website or portal.

In an embodiment, motion encoder 116 comprises a digital optical encoder. The digital optical encoder is configured to sense the speed of feeder 102 or transport device 104, as appropriate. Specifically, motion encoder 116 is adapted to convert the motion of feeder 102 or transport device 104 into a sequence of digital pulses. Processor 112 is capable of receiving the digital pulses to determine when print head 106 is appropriately above substrate stock 110, and more precisely, relative to the location on substrate stock 110 itself.

Optionally, print engine 106 can comprise a secondary optical sensor. The optical sensor is configured to detect when the substrate stock 110 is under the print head. The optical sensor is further adapted to transmit data to processor 112 such that, when combined with motion encoder 116 data, substrate stock 110 can be precisely related to a location under print head 118.

Print head 118 is configured to print ink or toner onto substrate stock 110. Print head 118 is adapted to receive print data from processor 112. Once substrate stock 110 is under print head 118, printed matter is imaged onto substrate stock 110 by print head 118. In a particular embodiment, print head 118 comprises an ink jet unit, such as, but not limited to, one commercially available from Xaar of Marietta, Ga., Dimatix, Inc. (Fujifilm) of Santa Clara, Calif., Fuji Xerox of Japan, Eastman Kodak of Rochester, N.Y., Hewlett Packard of Palo Alto, Calif., MemJet of San Diego, Calif., Kyrocera of Japan, and Epson of Long Beach, Calif. The resolution of print head 118 is suitable for producing high-quality, recognizable images on absorbent substrates. A suitable resolution is in a range of about 300-3600 dots per inch (DPI), and more particularly from about 600-1600 DPI.

Print head 118 can house printing medium appropriate for printing onto the chosen substrate stock 110. The medium can comprise a liquid or solid ink, toner, pigment, solvent-based inks, UV-curable or other radiation curable inks, e-beam curable inks, thermally curable inks, aqueous inks, metallic inks or pigments, or any of a variety of dye or pigment based inks or toners available or combinations thereof for use with digital printing systems. Suitable inks and toners are available from the print engine and/or print head manufactures, as well as other suppliers such as SUNCURE inks commercially available from Sun Chemical of Carlstadt, N.J., and UV curable inks commercially available from Flint Inks of St. Paul, Minn. Preferably, in the case of porous substrates such as napkins or tissues, the ink or toner does not significantly permeate the substrate, and rather stands on the surface of the substrate as a film to prevent or reduce bleeding of the ink or toner.

System 100 can optionally include one or more appropriate curing stations depending on the type of printing medium used. Suitable cure stations can include, for example, UV curing, LED lights, heat or IR curing, near infrared (NIR) curing, E-beam curing, dryers, microwave, and any suitable curing station or combinations thereof. The printing medium and curing station combination should be chosen such that the energy to cure the printing medium does not heat the substrate to such temperatures that the substrate ignites, distorts, discolors, or otherwise is destroyed.

Referring again to FIG. 1, deliverer 108 is configured to receive a printed substrate stock 110 from print engine 106 and transport substrate stock 110 to an operator. In an embodiment, deliverer 108 comprises a take-off conveyor adapted to allow an operator or automated device to take substrate stock 110 off of the conveyor and place substrate stock 110 in a shipping container. Deliverer 108 can optionally have the capability to stack, collate, sort, or otherwise process an order depending on the order details. In another embodiment, deliverer 108 comprises a portion of transport device 104.

Optionally, printed substrate stock 110 can include a printed identifier or mark that correlates the printed substrate stock with a customer order. Deliverer 108 can comprise an optical sensor for reading the identifier or data, such that deliverer 108 sorts or otherwise collates substrates 110 based on the customer order. This is particularly useful when multiple customer orders are being run in a single production run, i.e. gang run, such that manual sorting is not needed.

Figure 5:
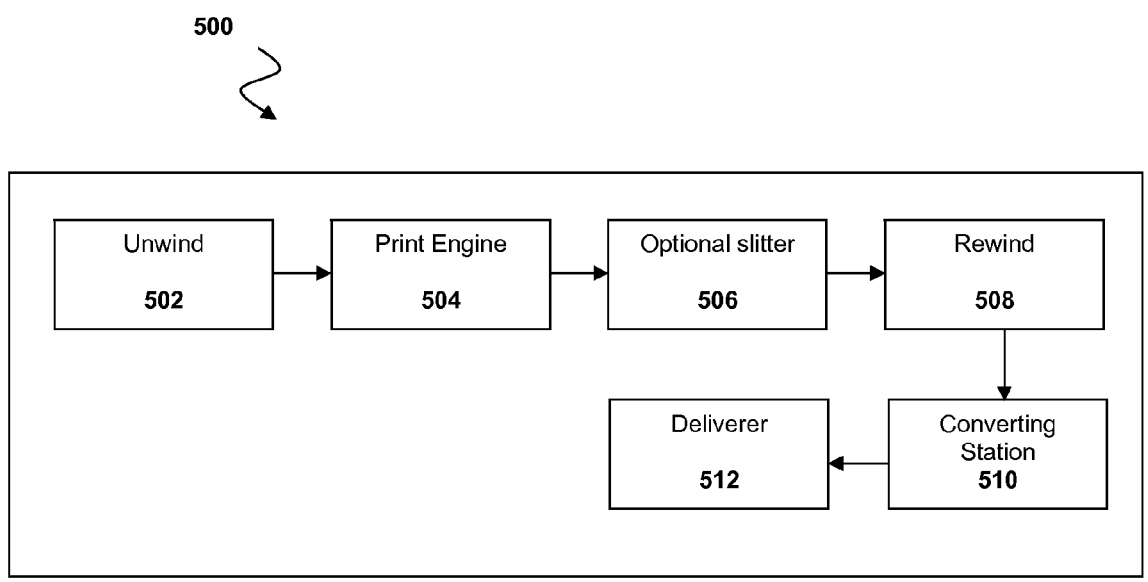
FIG. 5 is a block diagram of a web-based flexible substrate printing system according to an embodiment of the invention.

In another embodiment, and referring to FIG. 5, a substrate stock comprises unconverted stock, such as a web or roll of material to be printed. In such an embodiment, the printing system is placed upstream from a converting system that cuts, calendars and/or folds the web of substrate stock. More particularly, web printing system 500 generally comprises an unwind 502 for unwinding a web of substrate stock from a core, a one or more print stations or engines 504, one or more optional cure stations (not shown), and optional slitter 506 for slitting a web in a down-web or longitudinal direction thereby creating multiple webs, one or more rewinds 508 for taking up the printed web onto a core and to aid in tensioning the web, one or more converting stations 510 for converting or cutting the printed web into a plurality of printed articles, and one or more deliverers 512.

System 500 can operate at any of a variety of web speeds including 1 foot per minute (fpm) or less, 1-50 fpm or more, 50-150 fpm, or 150 fpm or more depending on the speed of print engines 504 without comprising quality. Web widths can be any of a selected variety of widths including 12 inches or less, 12-48 inches, or 48 inches or more. The web speed and/or web width should be selected so as to provide sufficient print quality including resolution and color saturation, while providing adequate tension such that the print quality is substantially consistent both down and cross web.

Unwind 502 includes a core receiving, rotatable shaft for mounting a roll of substrate thereon. System 500 further includes multiple tensions rolls (not shown) such that the web of substrate is substantially flat when entering one or more print stations 504. The one or more print engines 504 and optional cure stations are similar to print station 106 and cure stations described with respect to FIG. 1.

One or more optional slitters 506 are configured to cut or shear the initial web into multiple webs of narrower width. Optional slitters 506 can be placed before and/or after print station(s) 504. Slitter 506 can be of the conventional kind and can include straight and/or circular cutting blades. The cutting blades can be set to a desired width.

The printed and optionally slit stock substrate is then rewound on paper or plastic cores on one or more rewinds 508 positioned the exit side of system 500. Rewind 508 is similar to unwind 502, in that it comprises a rotatable shaft.

Once the printed substrate is rewound onto a core, it is then converted into one or more articles via one or more converting stations 510. Converting stations 510 can include, for example, slitters similar to slitter 506 (if web is to be slit after rewind operation rather than or in addition to slitting inline with printing), cutters such as guillotine, rotary die, laser, or any of a variety of cutting operations for cutting the substrate into individual articles, calendaring stations, embossing stations, and/or folding stations, or combinations thereof.

Deliverer 512 is similar to deliver 108 as described with respect to FIG. 1, and has the capability to stack, collate, sort, or otherwise process an order depending on the order details.

Similar to the embodiment in FIG. 1, the printed substrate stock can optionally include a printed identifier or mark that correlates the printed substrate stock with a customer order. Deliverer 512 can comprise an optical sensor for reading the identifier or data, such that deliverer 512 sorts or otherwise collates the articles based on the customer order. This is particularly useful when multiple customer orders are being run in a single production run, i.e. gang run, such that manual sorting is not needed.

Figure 3:
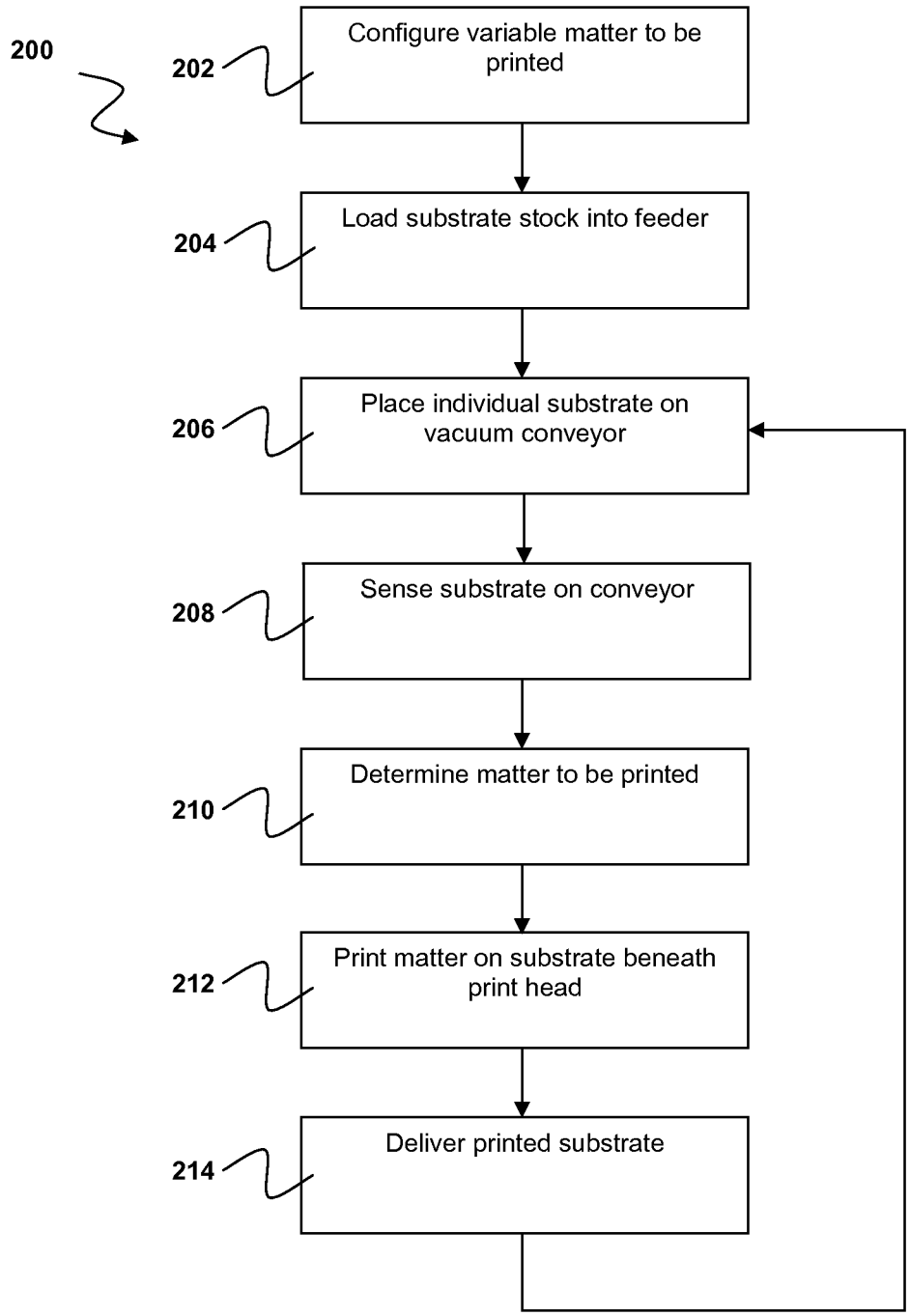
FIG. 3 depicts a method of printing variable data onto absorbent substrates, according to an embodiment of the invention.

In operation, referring to FIG. 3, a method of printing variable data onto a flexible substrate is depicted as 200, in an embodiment of the present invention. Method 200 comprises an iterative method of producing one or more printed set of substrates in a single production run. A single production run according to systems and methods of embodiments of the invention can be configured to efficiently and economically produce any number articles, including small set wherein the set of napkins comprises less than 1,000 napkins for example, less than 500, less than 100, less than 75, less than 50, less than 24, less than 10, or even a single article, or larger sets including more than 1,000 napkins, more than 2,500 napkins, more than 5,000, or more than 10,000 napkins. For non-limiting exemplary purposes only, the method 200 is being correlated to the system of FIG. 1; however the method is applicable to any of a variety of systems, including the web-based system of FIG. 5.

At 202, the variable matter to be printed in the production run is configured in the system. A user transmits the data to be printed to processor 112. As mentioned above, the data can vary between prints. Processor 112 stores this data in database 114.

At 204, substrate stock 110 is loaded into feeder 102. In an embodiment, feeder 102 can house all of the stock required for the production run. The stock can comprise the same or different substrates as will be described further below. In another embodiment, feeder 102 is refillable during the production run such that production can continue while feeder 102 is being refilled. In yet another embodiment, the feeder is an unwind, and the substrate stock is a web of flexible material (referring to FIG. 5, for example).

At 206, feeder 102 places an individual substrate onto transport device 104. The individual substrate is fixed in place due to the vacuum present throughout the perforations in the length of the belt or drum of transport device 104. Transport device 104 transports the individual substrate from feeder 102 to print head 118 of print engine 106.

At 208, while the individual substrate is traveling towards print head 118 along transport device 104, motion encoder 116 senses the speed of transport device 104. Motion encoder 116 transmits this data to processor 112. Optionally, a secondary optical sensor detects the substrate on the conveyor and transmits this data to processor 112.

At 210, processor 112 determines the matter to be printed for the particular substrate to be printed. Processor 112 reads database 114 at the appropriate location within database 114. In an embodiment, processor 112 sequentially reads a digital file and thereby reads in the matter to be printed. In another embodiment, processor 112 accesses a relational database with appropriate database-querying language to thereby read in the matter to be printed. Processor 112 transmits the matter to be printed to print head 118. For example, the variable data files uploaded in the database are ripped or otherwise converted to one or more print-ready files. This print stream is then sent to print head(s) 118. In one embodiment, multiple front-end rips are feeding print engine 106.

At 212, when processor 112 has calculated, based on the data received from motion encoder 116 and a secondary optical sensor, if desired, that the substrate is properly in place beneath print head 118, the matter is printed to the substrate with print head 118.

At 214, deliverer 108 receives the printed substrate from print engine 106. Deliverer 108 subsequently transports the printed substrate to a system operator, in an embodiment. The system operator is able to safely and effectively remove the printed substrate from deliverer 108. In another embodiment, deliverer 108 transports the printed substrate directly to a shipping container.

As shown in FIG. 3, method 200 is an iterative process. Assuming the steps just described constitute iteration (n) for the current substrate, at 214, method 200 returns to 206 in order to process the (n+1) iteration of the process, thereby handling the next subsequent substrate loaded into feeder 102, or the next location on a web of substrate. Of course, method 200 is depicted as it is for simplicity. Portions of the (n+1) iteration of method 200 can occur while the (n) iteration is occurring. Likewise, portions of the (n+2) iteration of method 200 can occur while the (n) and (n+1) iterations are occurring, and so on, depending on the length of transport and the intensity of printing.

Figure 4:
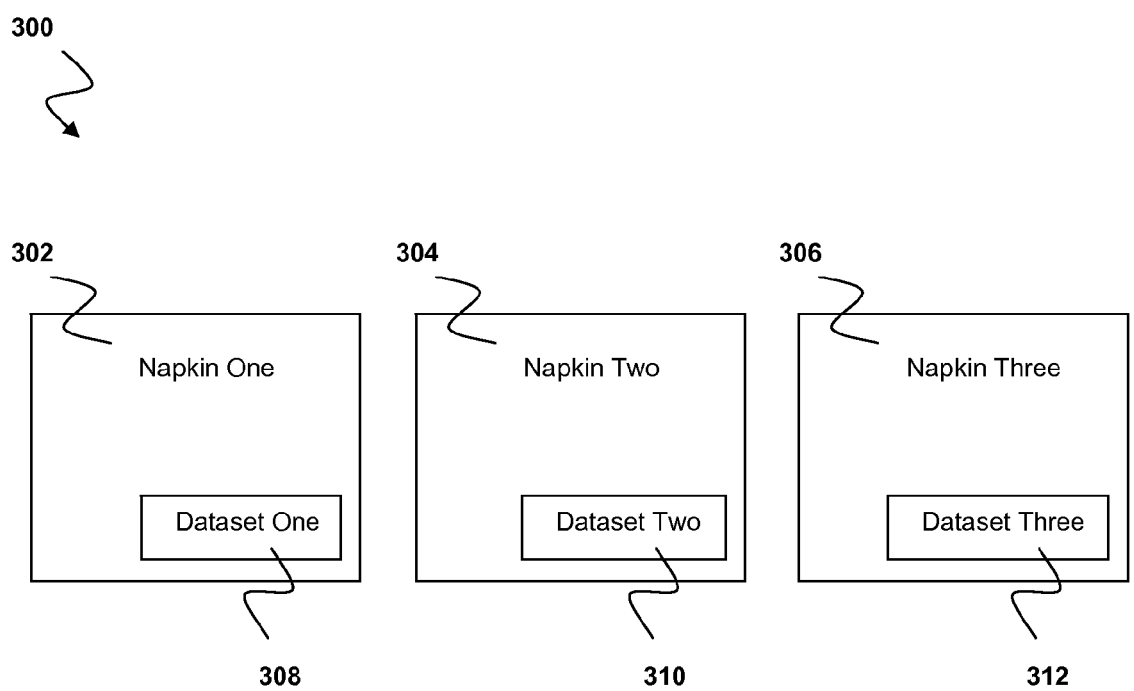
FIG. 4 is a block diagram of three substrates having varied printed data, according to an embodiment of the invention.

Referring to FIG. 4, a block diagram of three substrates having varied printed data, according to an embodiment of the invention, is shown at 300. The varied printed data on the napkins can be created by the embodiment of operation described above by method 200 and depicted by FIG. 3 in a single production run. The set 300 of substrates, as depicted, comprises napkin substrates having printed data on each napkin in the set. The set 300 of substrates comprises at least a first napkin 302, a second napkin 304, and a third napkin 306.

First napkin 302 comprises a first substrate having a dataset one 308 printed on the first substrate. Second napkin 304 comprises a second substrate having a dataset two 310 printed on the second substrate. Third napkin 306 comprises a third substrate having a dataset three 312 printed on the third substrate. As depicted, datasets one, two, and three 308, 310, and 312 are all unique from each of the other datasets 308, 310, and 312. Likewise, first, second, and third substrates 302, 304, 306 are all discrete from each of the other substrates. The first, second, and third substrates can be of the same material, size, color, shape, thickness, fold pattern, or can be different in any of the above-listed characteristics from each other. Each of the napkins 302, 304, and 306 can be from the same order, or part of a gang run (i.e. multiple and different orders).

The products, e.g. napkins, containing variable data manufactured according to embodiments of the present invention can utilized in a variety of ways and in a variety of settings. Some examples are described below, but there remains an infinite number of uses left to the consumer's imagination.

In one example, a set of napkins, such as cocktail or dinner napkins, for any of a variety of events, can be printed as game pieces, such that each napkin in the set includes a game, puzzle, riddle, joke, map, clue such as scavenger hunt clues, or the like. The set of napkins can have different data than the others, or alternatively, some can have the same static data except for one or a few unique or winning pieces that have variable data, the set being run within the same production run.

Other examples can include: (1) artistic substrates in which each piece includes instructions to draw a particular item and a space for drawing the item. The instructions can vary between each napkin in the set; (2) 2D barcodes, such as matrix-type codes (e.g. QR codes, DataMatrix, Maxi Code) or stacked bar-type codes (e.g. PDF417), barcodes, or tags in which each napkin in a set contains a unique 2D code, barcode, or tag different from the other napkins; (3) advertisement(s) on some or all of the napkins in the set, the advertisements containing variable data, such as different companies, services, and/or goods within the set, one such example being set forth in U.S. Patent Application Publication No. 2007/0164554, entitled ORDER FULFILLMENT SYSTEM AND METHOD FOR PRINTING PRODUCTS INCLUDING INDIVIDUALIZED INFORMATION, incorporated herein by reference in its entirety; (4) coupons with variable offers within a set of napkins including coupons with different offers within the set, and/or different companies, each offering their own goods and/or services within the set. Another example includes the use of personalized napkins in lieu of or in addition to place cards in which a guest sits at a table where their personalized napkin is located.

In one example, a 2D code, such as, but not limited to, a QR code, is printed on the napkin. A 2D barcode is a graphical image that stores information both horizontally and vertically. As a result of the two-dimensional construction, significantly greater storage is possible than with the capacity of a one-dimensional barcode. A device, such as a cell phone, reads the code by taking a picture of the code, scanning the code, or otherwise reading the code. The code acts as a key to gain access to any of an unlimited variety of sources, such as, for example, a database, a wireless network or WIFI enabled network, games, tools, contests, offers, coupons, or other otherwise secured information.

In one particular example, a 2D code is printed on each napkin of a set of napkins for an establishment, the QR code being the same or different on each napkin in a set. The 2D code is read or scanned using a device, such as a QR reader, scanner, or camera on a handheld device, such as a cell phone. The 2D code grants the user of the handheld device to a secured wireless network of the particular establishment. If the 2D code varies within the set of napkins, the recipient of a particular napkin may have a different level of access to the network than a recipient of another napkin having a different code. Additionally or alternatively, the 2D code can grant the user access to coupons or offers from the establishment, other products or services, games, contests, factoids, clues, credits, or any of a variety of otherwise secured information or combinations thereof. Other codes or tags that are capable of acting as access keys can also be contemplated.

Embodiments can also utilize features as discussed and disclosed in co-pending U.S. patent application Ser. No. 13/396,939 (published as U.S. Patent Application Publication No. 2012/0209688), entitled SYSTEMS AND METHODS FOR MULTI-PLATFORM TRANSACTION CARD ACCESS AND MANAGEMENT, and filed on Feb. 15, 2012, which is hereby incorporated by reference in its entirety.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, locations, configurations etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. A system for digitally printing a set of napkins in a single run, the system comprising:
    a database or files containing a set of data to be printed on a set of napkins in the single run, wherein the set of data comprises variable data to be printed on a napkin or napkins within the set of napkins in the single run;
    napkin stock comprising a plurality of discrete folded napkins, wherein the folded napkins include at least two adjacent ply;
    at least one digital printing engine adapted to print the napkin stock with a liquid ink at a printed resolution in a range from about 300 to about 3600 dots per inch, wherein the at least one digital printing unit is plateless or dieless;
    an optical sensor operably coupled to the at least one digital printing engine, the optical sensor being configured to detect when the napkin stock is positioned under one or more print heads of the at least one digital printing engine; and
    a transport device configured to transport the napkin stock to and from the at least one digital printing engine;
    wherein at least one of the individual napkins in the set of napkins printed in a single run contains printing different from printing on other individual napkins in the set of napkins printed in the single run, and
    wherein the liquid ink is configured to not significantly permeate the first ply of each discrete napkin to reduce bleeding of the liquid ink before drying, and wherein the second ply of each of the plurality of discrete folded napkins is substantially free of the liquid ink.

2. The system of claim 1, wherein the set of napkins comprises less than 75 napkins.

3. The system of claim 2, wherein the set of napkins comprises less than 50 napkins.

4. The system of claim 3, wherein the set of napkins comprises less than 10 napkins.

5. The system of claim 1, wherein the set of napkins comprises more than 1,000 napkins.

6. The system of claim 1, wherein each of the discrete napkins is substantially free of printing die imprints.

7. The system of claim 1, wherein the printed resolution is in a range from about 600 to about 1600 DPI.

8. The system of claim 1, wherein the plurality of discrete folded napkins includes a plurality of different types of substrate.

9. The system of claim 8, wherein each different type is different in at least one aspect including material, size, color, shape, thickness, and fold pattern.

10. The system of claim 1, wherein a weight of each discrete folded napkin allows the napkin to lie substantially flat during printing.

11. The system of claim 1, wherein the printed data of at least one of the individual napkins comprises a barcode or a QR code different from a barcode or a QR code printed on the other individual napkins in the set of napkins printed in the single run.

12. A system for digitally printing at least two sets of napkins in a single run, a first set of napkins having at least one of a different printed color or different printed indicia from a second set of napkins, the system comprising:
    a database or files containing a first set of data to be printed on the first set of napkins in the single run, and a second set of data different than the first set to be printed on the second set of napkins the single run;
    napkin stock comprising a plurality of discrete folded napkins, wherein the folded napkins include at least two adjacent ply;
    a digital printing engine configured to print the napkin stock with a plurality of liquid inks of different color in the single run at a printed resolution in a range from about 300 to about 3600 dots per inch, wherein the at least one digital printing unit is plateless or dieless; and
    a transport device configured to transport the napkin stock to and from the at least one digital printing engine, wherein the at least two sets of napkins are stacked at an end of the transport device after printing,
    wherein the liquid inks are configured to not significantly permeate a first ply of each discrete napkin to reduce bleeding of the liquid inks before drying, and wherein a second ply of each of the plurality of discrete folded napkins is substantially free of the liquid ink, and
    wherein the system is configured such that the liquid inks are substantially dry without an application of energy when stacked at the end of the transport device.

13. The system of claim 12, wherein each discrete napkin is substantially free of die or plate impressions.

* * * * *